United States Patent [19]

Kobayashi et al.

[11] Patent Number: 5,381,693
[45] Date of Patent: Jan. 17, 1995

[54] ULTRASONIC IMAGING APPARATUS WITH SYNTHESIZED FOCUS AND SETTING RANGE MARKINGS

[75] Inventors: Masaki Kobayashi, Utsunomiya; Toshiaki Takahashi, Tachikawa; Masato Nagura; Kazuhiko Hara, both of Utsunomiya, all of Japan

[73] Assignee: Canon Kabushiki Kaisha, Tokyo, Japan

[21] Appl. No.: 863,731

[22] Filed: Apr. 6, 1992

[30] Foreign Application Priority Data

Apr. 26, 1991 [JP] Japan ................. 3-124702

[51] Int. Cl.$^6$ ............... G01N 29/06; G01N 29/22
[52] U.S. Cl. ........................ 73/614; 73/629; 128/660.05; 128/660.08
[58] Field of Search .......... 73/597, 598, 599, 600, 73/606, 609, 611, 614, 618, 629, 646, 610; 128/660.05, 660.08

[56] References Cited

U.S. PATENT DOCUMENTS

| | | | |
|---|---|---|---|
| 4,010,634 | 3/1977 | Baumgartner | 73/620 |
| 4,135,406 | 1/1979 | Kretz | 73/620 |
| 4,141,347 | 2/1979 | Green et al. | 73/627 |
| 4,510,810 | 4/1985 | Kanda et al. | 73/606 |
| 4,608,868 | 9/1986 | Green | 73/606 |
| 4,953,405 | 9/1990 | Hara et al. | 73/602 |
| 4,980,865 | 12/1990 | Ishibashi et al. | 73/607 |
| 5,090,411 | 2/1992 | Higuchi | 128/660.05 |

FOREIGN PATENT DOCUMENTS 0057972  2/1990  Japan ................ 73/627

*Primary Examiner*—Tom Noland
*Assistant Examiner*—Rose M. Finley
*Attorney, Agent, or Firm*—Fitzpatrick, Cella, Harper & Scinto

[57] ABSTRACT

In an ultrasonic imaging apparatus, an object to be inspected is scanned while being irradiated by a generated ultrasonic beam. Echo signals from the object are received and a plane image and a cross-sectional image formed from the received echo signals are displayed. A marker indicating the focus position of the ultrasonic beam and a marker indicating the setting range of a detection gate are synthesized and displayed on the cross-sectional image. The plane image of the portion assigned by the focus position and the depth range on the cross-sectional image is obtained.

8 Claims, 3 Drawing Sheets

ULTRASONIC IMAGING APPARATUS WITH SYNTHESIZED FOCUS AND SETTING RANGE MARKINGS

BACKGROUND OF THE INVENTION

1. Field of the Invention

This invention relates to ultrasonic imaging apparatus which nondestructively observes an internal state, such as a defect or the like, within an object to be inspected using a focused untrasonic beam.

2. Description of the Prior Art

The configuration of such an ultrasonic imaging apparatus is shown, for example, in U.S. Pat. No. 4,953,405.

In a conventional procedure of nondestructive ultrasonic inspection, particularly by ultrasonic imaging, the focus point of a focused ultrasonic beam is first adjusted to a depth to be observed within an object to be inspected. Subsequently, in a plane display (C-mode) image, only an echo signal from a depth range to be observed is depicted while removing echo signals from the upper and lower surfaces of the object, and a time gate is set in order to configure an ultrasonic image.

According to the above-described operations, an ultrasonic echo signal and a time gate signal are displayed on the display surface of an oscilloscope. The operator gradually changes the distance between an ultrasonic transducer and the object, and adjusts the start point and time width of the time gate while observing the signals. Electronic-scanning-type ultrasonic medical diagnostic apparatuses are also known, wherein the focus point of an ultrasonic beam is displayed on a cross-section display (B-mode) image using a marker.

The above-described conventional appproaches, however, have the following problems.

(1) In, order to know the depth range within an object to be inspected to which an observed plane display image corresponds, or to provide an image of a predetermined depth range of the object, it is necessary to process an ultrasonic signal displayed on an oscilloscope, read the position of the signal on the time base, and calculate the actual depth.

(2) Iris also necessary to calculate to which depth within an object to be inspected the focus of an ultrasonic beam is adjusted by observing the waveform of an ultrasonic signal on an oscilloscope display in the same manner as in item (1).

(3) If the position of a defect within an object to be inspected cannot be predicted in advance, it is necessary to repeat the operations shown in items (1) and (2) in the range between the upper surface and the lower surface of the object.

Since the above-described operations require knowledge of ultrasonic techniques and are complicated, an expected image cannot be obtained if the operations are not adequately performed. Hence, such operations are disadvantageous in applying the ultrasonic imaging method.

SUMMARY OF THE INVENTION

It is an object of the present invention to provide an ultrasonic imaging apparatus which assigns the focus position of an ultrasonic beam and a depth range on a cross-sectional image, and which can obtain a plane image in the assigned conditions without requiring special technical knowledge.

The invention is directed to an ultrasonic imaging apparatus in which an object is scanned while being irradiated by an ultrasonic beam. A plane image and a cross-sectional image are formed from echo signals received from the object and markers indicating the focus position of the ultrasonic beam and the setting range of a detection gate are synthesized and displayed.

According to one aspect of the present invention, an ultrasonic imaging apparatus irradiates an ultrasonic beam onto an object to be inspected while scanning the beam, receives an echo signal from the object, and provides an image on a display. The apparatus includes a display for displaying a plane display image and a cross-section display image simultaneously or alternately on the display, and a control for displaying a marker indicating the focus position of the ultrasonic beam and a marker indicating a setting range of a detection gate on the cross-section display image.

In the ultrasonic imaging apparatus having the above-described configuration, by displaying the markers indicating the focus position of the ultrasonic beam and the position of the detection gate on the cross-section display image, the beam is focused on a predetermined depth within the object, and the plane display image in a prescribed depth range is obtained.

DESCRIPTION OF THE PREFERRED EMBODIMENTS

An embodiment of the present invention will now be explained in detail with reference to the drawings.

Figure 1:
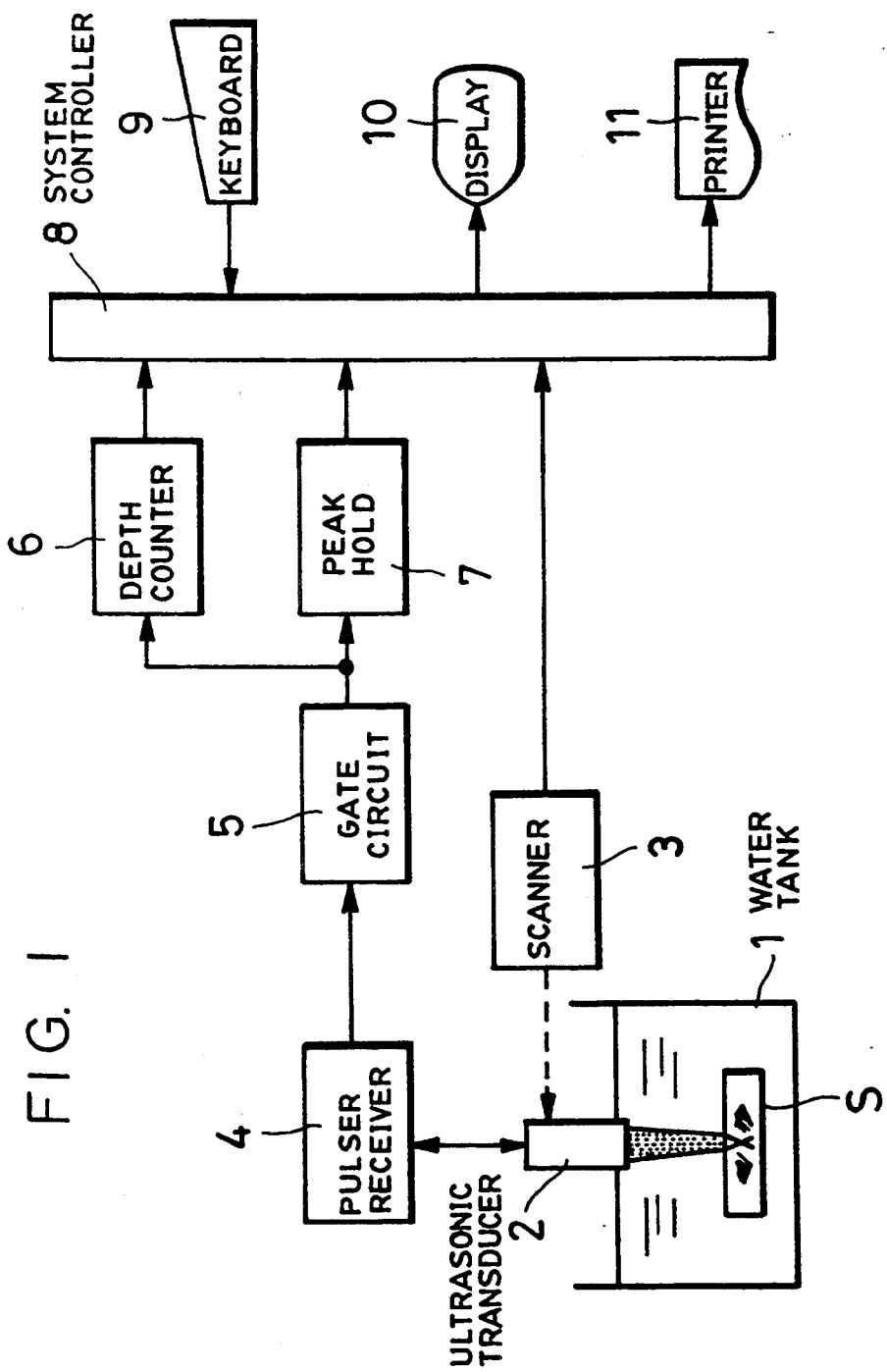
FIG. 1 is a diagram showing the configuration of an ultrasonic imaging apparatus according to an embodiment of the present invention.

FIG. 1 is a block diagram showing the configuration of an ultrasonic imaging apparatus according to the embodiment. An ultrasonic transducer 2 for transmitting and receiving ultrasonic pulses for an object (e.g., semiconductor chip) S to be inspected is placed within a water tank 1 and two-dimensionally scans the object S with a scanner 3. A pulser-receiver 4, which applies high-voltage pulses for transmitting ultrasonic waves to the ultrasonic transducer 2 and amplifies received signals, is connected to the ultrasonic transducer 2. The output of the pulser-receiver 4 reaches a gate circuit 5, whose output is connected to a depth counter 6 for depth detection in parallel with a peak hold circuit 7 for detecting signal intensity. The outputs of the depth counter 6 and the peak hold circuit 7 are connected to a system controller 8, to which a keyboard 9, a display 10 and a printer 11 are also connected.

An ultrasonic pulse generated from the ultrasonic transducer 2 by means of a high-voltage pulse generated by the pulser-receiver 4 is reflected at the surface and an internal boundary surface, such as a defect or the like, in the object S, and reflected waves are received by the transducer 2. Two kinds of time gates (i.e., a surface detection gate and a defect detection gate) are input from the keyboard 9 and are set in the gate circuit 5 as control signals of the system controller 8. The signals received by the transducer 2 are amplified by the pulser-receiver 4. Subsequently, by applying the time gates, a signal representing the wave reflected by the upper surface of the object S and a signal representing the wave reflected by the target internal boundary surface are extracted. By generating control signals, the system controller 8 provides the pulser-receiver 4 with a command to apply a high-voltage pulse, and transmits a counter reset command and a count start command to the depth counter 6. The depth counter 6 holds count values of output signals from the gate circuit 5. Output signals generated from the gate circuit 5 comprise the signal representing the wave reflected by the upper surface and the signal representing the wave reflected by the internal boundary surface. Since the signal representing the wave reflected by the upper surface is detected earlier, a first count value held by the depth counter 6 corresponds to a time from the transmission of the ultrasonic wave to the reception of the signal representing the wave reflected by the upper surface. The system controller 8 receives the count value t from the depth counter 6, and calculates the distance u between the ultrasonic transducer 2 and the object S as $u = V \cdot t/2$ based on the sound velocity V in water input from the keyboard 9.

Figure 2:
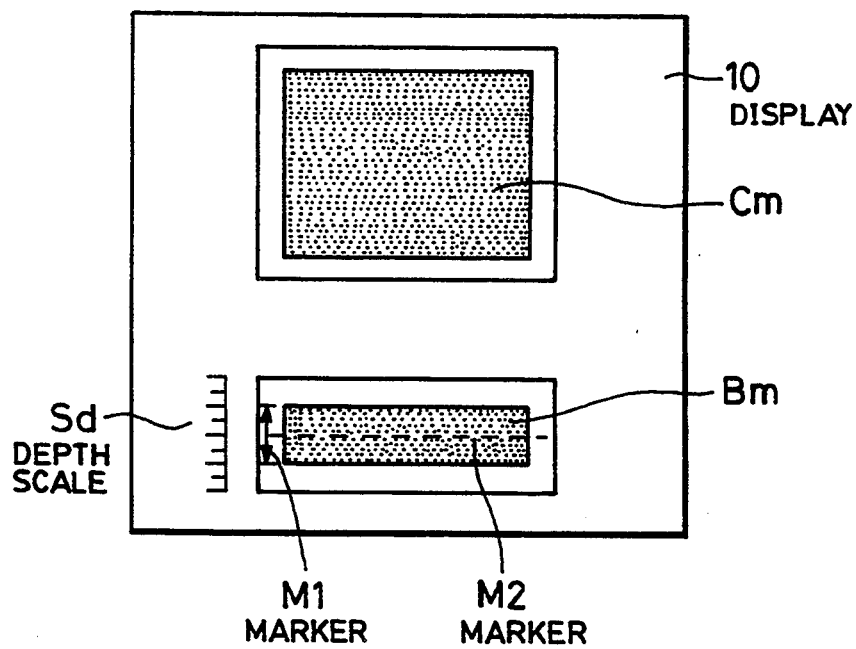
FIG. 2 is a diagram illustrating an example of an image display.

FIG. 2 shows an example of a display on the display 10. A plane display image Cm shown in an upper portion is displayed by receiving the output of the peak hold circuit 7 in the system controller 8, calculating the intensity of the signal, making the intensity correspond to a color or a luminance, and combining the intensity data with positional information from the scanner 3. A cross-section display image Bm is displayed by receiving the output of the depth counter 6 in the system controller 8, calculating the depth using the sound velocity of the ultrasonic wave input from the keyboard 9, and combining the calculated data with positional information from the scanner 3. The plane display image Cm and the cross-section display image Bm may be simultaneously displayed or alternately displayed.

Marker M1 indicating the defect detection gate is synthesized and displayed by calculating information output from the system controller 8 to the gate circuit 5 as a control signal to correspond to the depth position in the cross section display image Bm. Marker M2 indicating the position of the focus point is synthesized and displayed by calculating the depth position of the focus point of the ultrasonic beam within the object S from the output of the depth counter 6, the sound velocity of the ultrasonic wave input from the keyboard 9, and the focal length of the ultrasonic transducer 2.

Figure 3:
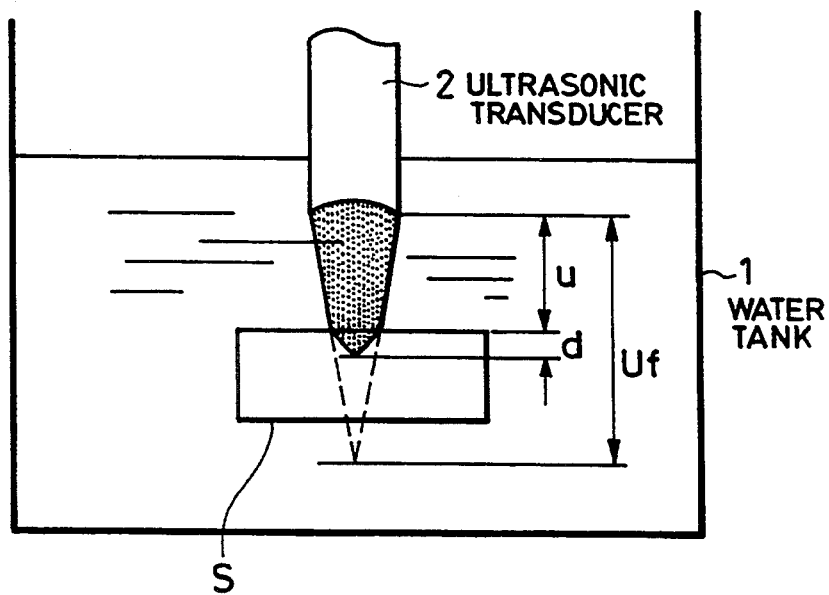
FIG. 3 is a diagram illustrating focus point adjustment.

That is, as shown in FIG. 3, the depth d from the surface of the object S of the focus point of the ultrasonic beam within the object S is calculated according to $d = (V/Vs) \cdot (Uf - u)$ by inputting the focal length Uf of the ultrasonic transducer 2 and the sound velocity Vs within the object S from the keyboard 9, and is displayed on the display 10 as the marker M2 indicating the position of the focus point. A depth scale Sd is displayed at a side of the cross section display image Bm.

The marker M2 indicating the position of the focus point is displayed at a position corresponding to the depth d in the vertical direction of the cross section display image Bm, that is, in the direction of depth. The depth counter 6 also holds a second count value corresponding to the signal of the wave reflected by the internal boundary surface. The difference between the second and first count values corresponds to a time from the reception of the signal representing the wave reflected by the upper surface to the reception of the signal representing the wave reflected by the internal boundary surface. The system controlled 8 calculates the depth d' of the internal boundary as $d' = (\frac{1}{2})Vs \cdot \Delta t$ from the difference $\Delta t$ between the second and first count values, and the sound velocity within the object S input from the keyboard 9, and displays the calculated depth d' by combining it with positional information from the scanner 3 as the cross-section display image Bm.

The peak hold circuit 7 holds the value of the maximum amplitude obtained by a circuit for detecting the amplitude of the signal representing the wave reflected by the internal boundary surface within the output signals of the gate circuit 5. The system controller 8 receives the amplitude value output from the peak hold circuit 7, makes the intensity of the signal correspond to a color or a luminance, combines the intensity data with positional information from the scanner 3, and displays depth information indicated by the marker M1 indicating the defect detection gate as the plane display image Cm. The marker M1 displays the defect detection gate on the display 10 from among time gates set in the gate circuit 5. The marker M1 also displays the corresponding depth range in the direction of depth in the cross section display image Bm in the same manner as marker M2. The form of display of these two kinds of markers M1 and M2 may be arbitrarily selected, such as a cursor line, an arrow or the like, as shown in FIG. 2, provided that the marker has a shape, a color and a luminance which can be discriminated from those of the ultrasonic image. The positions of the defect detection gate and the focus point in the vertical direction, that is, in the z-axis direction of the scanner 3, may be set or changed on a real-time basis even during a scanning operation of the scanner 3.

In the present embodiment, the position of the focus point is set by an upward-arrow key and a downward-arrow key provided on the keyboard 9. That is, if the operator depresses the upward-arrow key, the scanner 3 rises, and the marker M2 indicating the position of the focus point rises on the display Bm. If the downward-arrow key is depressed, the scanner 3 descends, and the marker M2 descends on the display Bm. The position of the defect detection gate may also be easily set using other keys. Since the system controller 8 immediately transmits control signals to the gate circuit 5 and the scanner 3 in accordance with the setting of the positions of the defect detection gate and the focus point, the setting is changed during a scanning operation of the scanner 3, whereby the plane display image Cm is changed on a real-time basis. Although, most preferably, the operator may set the both positions of the defect detection gate and the focus point, the operator need only set one of these positions.

As described above, by arranging the marker M1 indicating the defect detection gate and the marker M2 indicating the position of the focus point on the same scale, i.e., a depth scale, and synthesizing and displaying these markers with the cross section display image Bm, it is possible to easily operate the apparatus to obtain a focused plane display image Cm. Hence, specialized technical operation knowledge is not required by the operator.

Figure 4:
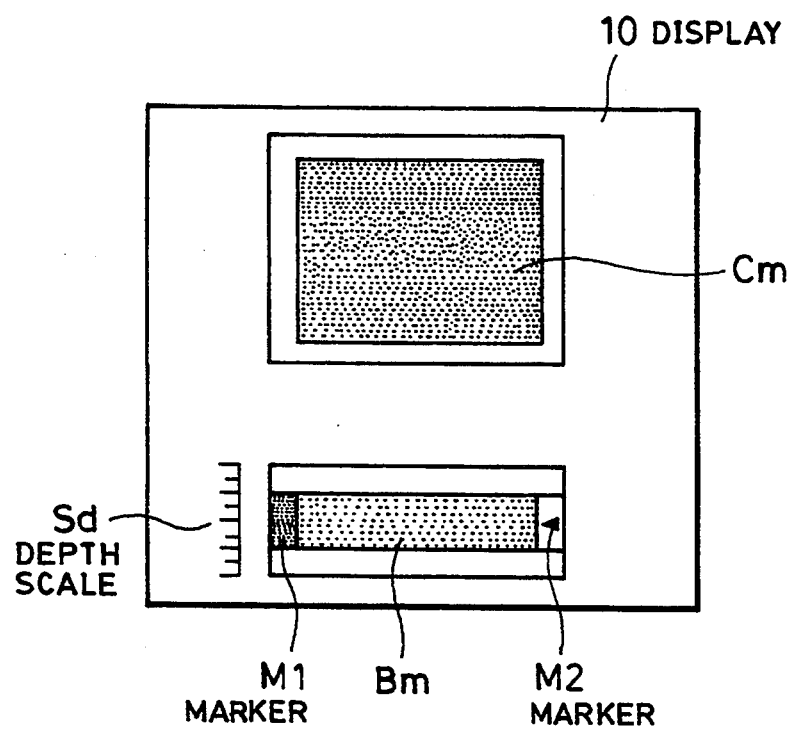
FIG. 4 is a diagram illustrating another example of an image display.

Although, in the above-described embodiment, the depth of the focus point and the position of the gate are displayed by an arrow and a line separate from the ultrasonic image, the present invention is not limited to such an approach. For example, in FIG. 4, display is performed so that the depth of the focus point and the position of the gate can be discriminated by performing brilliance modulation of the ultrasonic image itself or changing the display color. That is, the marker M1 is displayed by changing its luminance, and the marker M2 is displayed as a triangle mark.

The method of displaying the cross section display image Bm may use a redrawing mode wherein the image is updated for every scanning operation of the focused ultrasonic beam, or an overdrawing mode over the entire scanning period. Alternatively, these modes may be switched. At a first inspection of the object S, the thickness of the object S may be input, inspection may be performed by automatically setting the defect detection gate in the entire interval between echo signals from the upper surface and the lower surface of the object S. Subsequently, the defect detection gate may be set again while observing the image as in the above-described embodiment.

If the defect detection gate or the focus point of the ultrasonic beam are set outside the depth range between the upper surface and the lower surface of an object to be inspected, a warning signal may be issued, or the setting may not be accepted. The warning signal may, for example, be a character message on the display 10. Alternatively, the marker M1 or M2 may be flashed, the color of the marker M1 or M2 may be changed, or a method wherein voice is utilized or the like may be utilized.

In the above-described ultrasonic imaging apparatus, the operator can directly perform focusing and the setting of a time gate, which have previously been performed indirectly while observing a waveform on an oscilloscope, while visually confirming the operation on a cross section display image. Hence, it is possible to focus on a predetermined depth in an object to be inspected exactly, and to obtain an image from ultrasonic data in a predetermined depth range in a simple manner. Accordingly, the apparatus can be easily utilized even by an operator who does not have specialized technical knowledge.

The present invention is not limited to inspection of semiconductor chips, but may, of course, be also applied to nondestructive inspection of various objects, ultrasonic diagnosis in the medical field, and the like.

What is claimed is:

1. An ultrasonic imaging apparatus, comprising:
    means for generating an ultrasonic beam;
    scanning means for scanning an object to be inspected while irradiating the ultrasonic beam;
    means for receiving echo signals from the object;
    display means for displaying a plane image and a cross-sectional image formed based on said received echo signals; and
    synthesizing means for synthesizing a marker indicating a focus position of the ultrasonic beam and a marker indicating a setting range of a detection gate on said displayed cross-sectional image.

2. An apparatus according to claim 1, wherein said scanning means two-dimensionally scans the ultrasonic beam relative to the object.

3. An apparatus according to claim 1, further comprising means for changing at least one of the focus position of the ultrasonic beam and the detection gate.

4. An apparatus according to claim 3, wherein said detection gate is set so as to pass a signal present between an upper-surface signal and a lower-surface signal from among the echo signals from the object, and not to pass said upper-surface signal and said lower-surface signal.

5. An apparatus according to claim 3, further comprising means for generating a signal indicative of a warning or non-acceptance of a setting if at least one of said two markers is set outside a depth range between an upper surface and a lower surface of the object.

6. An apparatus according to claim 1, wherein said display means includes means for operating in at least one of a mode of updating said cross-sectional image for every scanning period of the ultrasonic beam, and a mode of overdrawing said cross-sectional image over the scanning period.

7. An apparatus according to claim 1, wherein the object to be inspected comprises a semiconductor chip.

8. An ultrasonic imaging method comprising the steps of:
    generating an ultrasonic beam;
    scanning an object to be inspected while irradiating the ultrasonic beam;
    receiving echo signals from the object;
    displaying a plane image and a cross-sectional image formed responsive to the received echo signals; and
    synthesizing, on the displayed cross-sectional image, a marker indicating a focus position of the ultrasonic beam and a marker indicating a setting range of a detection gate.

* * * * *

UNITED STATES PATENT AND TRADEMARK OFFICE
CERTIFICATE OF CORRECTION

PATENT NO. : 5,381,693
DATED : January 17, 1995
INVENTOR(S) : MASAKI KOBAYASHI, ET AL.

It is certified that error appears in the above-indentified patent and that said Letters Patent is hereby corrected as shown below:

COLUMN 1

```
Line 37, "In," should read --In--.
Line 44, "Iris" should read --It is--.
```

Signed and Sealed this

Fourth Day of April, 1995

Attest:

BRUCE LEHMAN

Attesting Officer        Commissioner of Patents and Trademarks